United States Patent [19]

Tsukada

[11] Patent Number: 5,683,369
[45] Date of Patent: Nov. 4, 1997

[54] BELLOWS TYPE CONTAINER CHARGED WITH LIQUID MEDICINE

[75] Inventor: Osamu Tsukada, Nagano-ken, Japan

[73] Assignee: Tsukada Medical Research Co., Ltd., Tokyo, Japan

[21] Appl. No.: 406,927

[22] PCT Filed: Apr. 12, 1994

[86] PCT No.: PCT/JP94/00613

§ 371 Date: Mar. 27, 1996

§ 102(e) Date: Mar. 27, 1996

[87] PCT Pub. No.: WO95/27522

PCT Pub. Date: Oct. 19, 1995

[51] Int. Cl.[6] ............................................. A61M 5/178
[52] U.S. Cl. ..................... 604/212; 604/216; 604/133
[58] Field of Search ............................. 604/212, 213, 604/216, 415, 403, 408, 131, 133

[56] References Cited

U.S. PATENT DOCUMENTS

| | | | |
|---|---|---|---|
| 2,950,717 | 8/1960 | Bouet | 604/216 X |
| 3,017,883 | 1/1962 | Dickinson, Jr. | 604/415 X |
| 3,712,295 | 1/1973 | Kline | 604/216 X |
| 3,892,237 | 7/1975 | Steiner | 604/216 X |
| 4,296,071 | 10/1981 | Weiss et al. | 604/216 X |
| 4,392,860 | 7/1983 | Huck et al. | 604/212 |
| 4,411,656 | 10/1983 | Cornett, III | 604/212 |
| 4,642,088 | 2/1987 | Gunter | 604/216 X |
| 5,342,329 | 8/1994 | Croquevielle | 604/213 X |

FOREIGN PATENT DOCUMENTS

| | | |
|---|---|---|
| 0295504 | 12/1988 | European Pat. Off. . |
| 0452912 | 10/1991 | European Pat. Off. . |
| 0473781 | 3/1992 | European Pat. Off. . |
| 0509754 | 10/1992 | European Pat. Off. . |

*Primary Examiner*—Sam Rimell
*Attorney, Agent, or Firm*—Sughrue, Mion, Zinn, Macpeak and Seas

[57] ABSTRACT

A bellows type container charged with liquid medicine widens a range of use. In a bellows type container (1) charged with liquid medicine, a bellows type body (11) is provided on its one end with an outlet portion (12) for liquid medicine and on its other end with a one-way valve (13) and a foldable hook (14) the liquid medicine is injected into and ejected from said bellows type body (11) through the one-way valve (13).

2 Claims, 1 Drawing Sheet

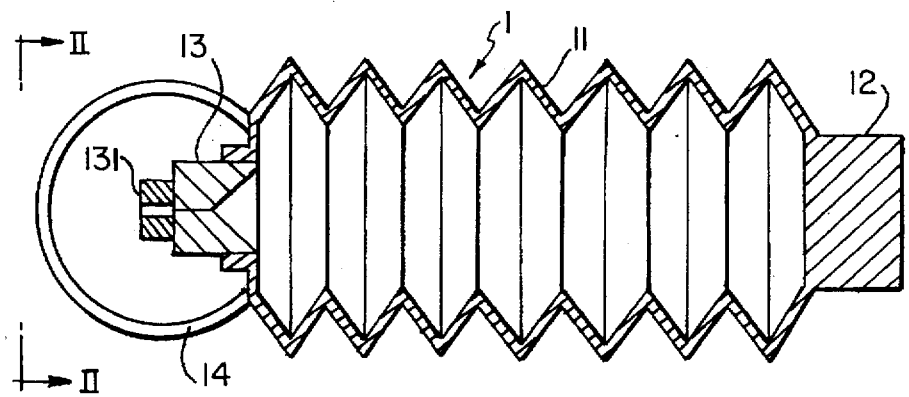
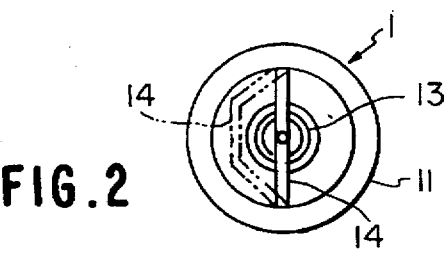
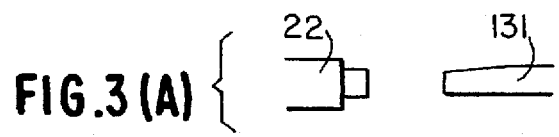
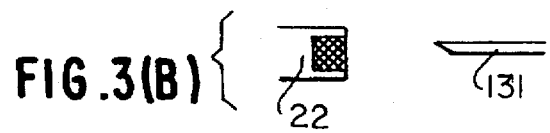
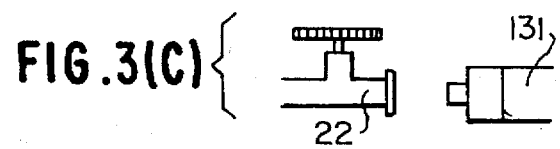
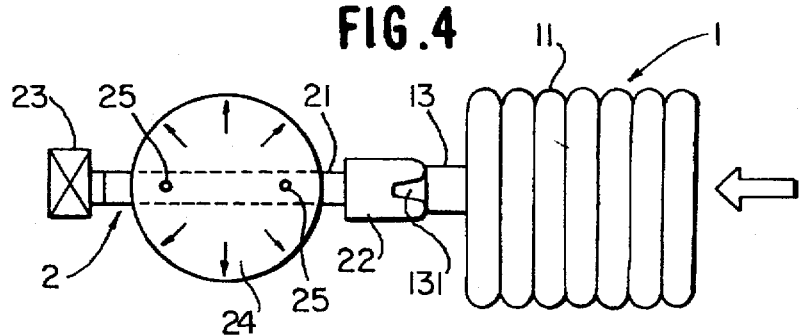

BELLOWS TYPE CONTAINER CHARGED WITH LIQUID MEDICINE

[TECHNICAL FIELD]

This invention relates to a bellows type container charged with liquid medicine.

[BACKGROUND ART]

There is in a part of a liquid transfusion set a bellows type container charged with liquid medicine (for example, physiological saline, grape sugar, antibiotic substance, calmative, analgesic, heparin, nitroglycerin solution and the like).

Heretofore, since such a kind of container is provided with only an outlet for liquid medicine on its one end, its object of use was limited.

On the other hand, there has been a continuous injector for liquid medicine (Japanese Patent No. 1384289) developed by the present applicant. This injector includes an inlet portion for liquid medicine, an outlet portion for liquid medicine, and a balloon which connects the inlet portion to the outlet portion. Liquid medicine injected in the balloon flows out through the outlet portion for a long period of time.

However, this continuous injector for liquid medicine requires an additional injector for injecting liquid medicine into the balloon of the former injector. This operation is troublesome and maintenance of a pair of injectors is inconvenient. Thus, the present applicant has proposed "a continuous injector for liquid medicine with a bellows type container" (Japanese Utility Model Publication No. 6-7722 (1994)), in which the continuous injector for liquid medicine is effectively united to a conventional bellows type container charged with liquid medicine.

However, in this injector, in the case of using only the container, handling of the container is difficult on account of the obstructive injector.

[DISCLOSURE OF INVENTION]

An object of the present invention is to provide a bellows type container charged with liquid medicine which can be used as usual a conventional liquid medicine container and a special tool such as a continuous injector for liquid medicine.

In a bellows type container charged with liquid medicine, a bellows type body is provided at one end with an outlet portion for liquid medicine and at its other end with a one-way valve and a foldable hook. The liquid medicine is injected into and ejected from the bellows type body through the one-way valve.

In the bellows type container charged with liquid medicine in accordance with the present invention, under a normal use the hook is hung on a support table and a needle for ejecting the liquid medicine and a needle for communicating with the atmosphere are pierced through the outlet portion to eject the liquid medicine.

Under a special use for a special tool such as the continuous injector for liquid medicine, the one-way valve is connected to an inlet portion of the special tool and the liquid medicine in the container is flowed into the special tool by compressing a bellows type body. When compression of the bellows type body is interrupted, the body maintains its compressed state.

[BRIEF DESCRIPTION OF DRAWINGS]

FIG. 1 is a longitudinal sectional view of a bellows type container charged with liquid medicine in accordance with the present invention;

FIG. 2 is a front elevational view taken along lines II—II in FIG. 1;

FIG. 3 is an explanatory view of coupling constructions; and

FIG. 4 is an explanatory view of an example of utilizing the container of the present invention.

[BEST MODE FOR CARRYING OUT THE INVENTION]

Embodiments of a bellows type container charged with liquid medicine in accordance with the present invention will be explained below by referring to FIGS. 1 to 4.

As shown in FIGS. 1 and 2, in the bellows type container 1 charged with liquid medicine of the present invention a bellows type body 11 is provided on its one end with an outlet portion 12 for liquid medicine and its other end with a one-way valve 13 and a foldable hook 14. On the other hand, liquid medicine can be injected into and ejected from the body 11 through the one-way valve 13.

The bellows type body 11 is made of a flexible material (for example, polyethylene, polypropylene or the like). A given liquid medicine is injected in the container 1.

The outlet portion 12 for liquid medicine is integrally formed with the body 11 or made of synthetic rubber or the like independent on the body 11.

The one-way valve 13 can open in a direction for ejecting liquid medicine in the container 1 outwardly but closes under a normal state. However, as described below, preferably a needle or the like can pierce the one-way valve 13 inwardly. Preferably, the one-way vale 13 can open when the valve 13 is pushed inwardly. For example, a duckbill valve or the like is preferable as such a one-way valve.

The one-way valve 13 is provided at its outlet with a usual coupling portion 131.

An explanation of an example of use as a usual bellows type container charged with liquid medicine is omitted.

An example in which a continuous injector 2 for liquid medicine described above is coupled to the container 1 of the present invention to be used as a special tool will be explained below.

The continuous injector 2 for liquid medicine, as shown in FIG. 4, is provided on opposite ends of a cylindrical body 21 with an inlet portion 22 for liquid medicine and an outlet portion 23 for liquid medicine. A balloon 24 is attached to an outer periphery of the cylindrical body 21. An interior of the balloon 24 is communicated with an interior of the cylindrical body 21 through a communication hole 25.

The cylindrical body 21 may be omitted and the inlet portion 22 and outlet portion 23 may be directly interconnected.

The inlet portion 22 is provided with a check valve (not shown) which prevents injected liquid medicine from flowing in a reverse direction. The balloon 24 is made of an elastic material and can accommodate a given amount of liquid medicine. The outlet portion 23 is provided with a control path (not shown) which controls an outflow period of time for liquid medicine.

The inlet portion 22 of the injector 2 is coupled to the coupling portion 131 of the container 1, as shown in FIG. 3, through a check valve and a male lure or a male lock (A); and injection port and a needle (B); or a stop cock and a male lure or a male lock (C).

In the case of using the bellows type container 1 for liquid medicine, the hook 14 is folded (FIG. 2). Upon using the continuous injector 2 for liquid medicine, as shown in FIG. 4, the bellows type body 11 is manually pushed to insert the coupling portion 131 into the inlet portion 22 of the injector 2. The body 11 is then manually compressed so that all of the liquid medicine in the container 1 is transferred into the balloon 24 of the injector 2.

Next, after the container 1 is detached from the injector, a needle not shown is pierced through the outlet portion 23 of the injector 2 to carry out a usual medical treatment.

[INDUSTRIAL APPLICABILITY]

According to the present invention, it is possible not only to widen a range of use for a bellows type container charged with liquid medicine, to simplify and enhance conventional medical treatments but also to minimize a residual amount of liquid medicine in the container. In particular, the container of the present invention is effective for a first-aid treatment of emergency patients.

I claim:

1. A bellows type container charged with liquid medicine comprising:

a bellows type body defining a chamber therein;

an outlet portion provided at a first end of said bellows-type body a one way valve provided at a second, opposite end of said bellows-type body; and a foldable hook secured to said bellows-type body, wherein the liquid medicine is injected into and ejected from said bellows type body through said one-way valve, wherein said bellows-type container is operable in first and second modes, in said first mode said one-way valve is connectable to an auxiliary tool through said one-way valve so that the liquid medicine previously injected into said chamber is ejected into said auxiliary tool and in said second mode an auxiliary needle is insertable through said outlet portion in fluid communication with said chamber such that the liquid medicine can be ejected from said chamber via said needle.

2. The bellows-type container of claim 1, wherein said lock is located at said second end.

* * * * *